United States Patent
Müller et al.

(10) Patent No.: US 9,949,665 B2
(45) Date of Patent: Apr. 24, 2018

(54) METHOD, SYSTEM AND DEVICE FOR POSITIONING AN IMPLANT

(75) Inventors: Heiko Müller, München (DE); Mario Schubert, Poing (DE); Martin Haimerl, Gilching (DE)

(73) Assignee: Brainlab AG, Munich (DE)

( * ) Notice: Subject to any disclaimer, the term of this patent is extended or adjusted under 35 U.S.C. 154(b) by 824 days.

(21) Appl. No.: 14/125,722

(22) PCT Filed: Jun. 17, 2011

(86) PCT No.: PCT/EP2011/060101
§ 371 (c)(1),
(2), (4) Date: Dec. 12, 2013

(87) PCT Pub. No.: WO2012/171577
PCT Pub. Date: Dec. 20, 2012

(65) Prior Publication Data
US 2014/0114179 A1 Apr. 24, 2014

(51) Int. Cl.
*A61B 5/00* (2006.01)
*A61B 5/06* (2006.01)
(Continued)

(52) U.S. Cl.
CPC .............. *A61B 5/067* (2013.01); *A61B 34/20* (2016.02); *A61F 2/4603* (2013.01);
(Continued)

(58) Field of Classification Search
CPC .... A61B 2017/00477; A61B 2034/105; A61B 2034/2048; A61B 2034/2055;
(Continued)

(56) References Cited

U.S. PATENT DOCUMENTS

| 7,559,931 B2 | 7/2009 | Stone |
|---|---|---|
| 2004/0243148 A1 | 12/2004 | Wasielewski |

(Continued)

FOREIGN PATENT DOCUMENTS

DE 4225112 C1 12/1993

OTHER PUBLICATIONS

International Search report for PCT/EP2011/060101 dated Mar. 30, 2012.
"Computer Assisted Surgery", Wikipedia, https://en.wikipedia.org/wiki/Computer-assisted_surgery, Apr. 25, 2017.

*Primary Examiner* — Ruth S Smith
(74) *Attorney, Agent, or Firm* — Tucker Ellis LLP

(57) ABSTRACT

The present invention relates to a method for measuring or verifying the position of a medical implant located in an anatomical body part(s) and/or structure(s) relative to the body part(s) and/or structure(s) or specific points, landmarks or planes of the same, wherein a device is provided which has an at least partially known or previously determined geometry or at least partially known dimensions and is connected to the medical implant; positional or landmark information regarding the anatomical body part(s) and/or structure(s) is acquired; the position of the medical implant is calculated using a navigation system and a reference structure which is or can be connected to the device; and the calculated position of the medical implant is related to or compared with the acquired positional or landmark information regarding the anatomical body part(s) and/or structure(s) in order to measure or verify the position of the medical implant within or relative to the anatomical body part(s) and/or structure(s).

11 Claims, 1 Drawing Sheet

(51) Int. Cl.
 *A61B 17/00* (2006.01)
 *A61F 2/46* (2006.01)
 *A61B 90/00* (2016.01)
 *A61B 34/20* (2016.01)
 *A61B 34/10* (2016.01)

(52) U.S. Cl.
 CPC .............. *A61B 2017/00477* (2013.01); *A61B 2034/105* (2016.02); *A61B 2034/2048* (2016.02); *A61B 2034/2055* (2016.02); *A61B 2034/2068* (2016.02); *A61B 2090/0818* (2016.02); *A61F 2/4609* (2013.01)

(58) Field of Classification Search
 CPC .... A61B 2034/2068; A61B 2090/0818; A61B 34/20; A61B 5/067; A61F 2/4603; A61F 2/4609
 See application file for complete search history.

(56) References Cited

U.S. PATENT DOCUMENTS

| | | | | |
|---|---|---|---|---|
| 2005/0148843 | A1* | 7/2005 | Roose | A61B 17/17 600/407 |
| 2006/0287613 | A1* | 12/2006 | Amiot | A61B 34/20 600/587 |
| 2009/0099570 | A1 | 4/2009 | Paradis et al. | |
| 2009/0209851 | A1* | 8/2009 | Blau | A61B 17/1703 600/426 |

* cited by examiner

METHOD, SYSTEM AND DEVICE FOR POSITIONING AN IMPLANT

RELATED APPLICATION DATA

This application is a national phase application of International Application No. PCT/EP2011/060101 filed Jun. 17, 2011 and published in the English language.

The present invention relates to a method, a system and a device for positioning an implant, such as a cup implant, inside the acetabulum, or a stem into the femur or femoral canal, for example during total hip arthroplasty, and in particular to a method for verifying an implant position in a pinless or minimally invasive procedure.

Although the invention is described hereinafter with respect to a cup implant as an exemplary embodiment, it has to be understood that the invention also relates to and can be practiced with other implants to be seated in other locations or anatomical structures, such as a stem in the femur. The invention can also be applied to more than one implant within one surgery, e.g. for the cup implant and the stem. Further on, the verification of the implant position can be related to one particular anatomical structure, e.g. cup orientation in relation to the pelvic bone, or the entire anatomical structure (combination of different body parts), e.g. range-of-motion of a hip joint which is related to the relative position between pelvis and femur.

Computer-aided surgery (CAS) systems assist surgeons in different types of surgery such as total hip replacement (THR), total knee replacement (TKR) and neurosurgery. In THR, the patient is usually positioned on his side or back during surgery, so that the surgeon can work on the acetabulum or the femoral head. A surgeon usually starts a THR by firstly working on the acetabulum, including the step of preparing the acetabulum in order to subsequently insert an acetabular cup implant. This acetabular cup implant has to be properly positioned, preferably with respect to predefined reference planes of the pelvis such as the anterior pelvic plane (APP) and the mid-sagittal plane (MSP). A trial cup is usually inserted first, in order to check the proper alignment and fit of the cup within the acetabulum, and then removed in order to insert the final cup, i.e. the actual implant, which is to be subsequently connected to the femoral implant in order to form an artificial hip joint.

However, if the femoral or acetabular cup implant is misaligned, there is a significant risk of dislocation of the femur or of impingement or excessive wear between the femoral implant neck and the acetabular cup of the pelvis, which may subsequently lead to discomfort for the patient. Thus, if the trial implant or the final implant is not properly inserted, the surgeon removes the implant and re-positions it, until the implant is properly aligned and installed.

Numerous methods for aiding in placing an implant are known.

In accordance with one well-known method, an acetabular implant is connected to a trackable reference, and another trackable reference is secured to the pelvis, as for example shown in US 2009/0099570 A1.

Another known method uses elastic bands attached to the femur; these, however, only aid in roughly positioning the implant.

In accordance with another method, a reference array is fitted into the sawing slots of both the tibial and femoral cutting block adaptors (CBA), and a surgeon performs a registration procedure using an additional pointer device.

In accordance with another method, rigid reference arrays are attached to the bone at a bony region which is subsequently re-sected.

In accordance with another method, a medical instrument to be aligned is aligned with respect to a target point, wherein the spatial position of the instrument to be aligned is determined and tracked by means of a medical tracking system, wherein the target point is indicated by a freely movable positioning instrument or pointer, the position of which is likewise determined and tracked by means of the medical tracking system, and the instrument to be aligned is then aligned with respect to the target point with the aid of a medical navigation procedure which is associated with the tracking system.

It is an object of the invention to provide a method, a system and a device for correctly placing an implant which reduces invasiveness while providing greater accuracy.

This object is solved by the subject-matter of the independent claims. Advantageous features, embodiments and aspects of the invention are disclosed in the following and included in the subject-matter of the dependent claims. Different advantageous features can be combined wherever technically sensible and feasible. In particular, a feature of one embodiment which has the same or a similar function to another feature of another embodiment can be exchanged. In particular, a feature of one embodiment which supplements another function of another embodiment can be added to said other embodiment.

Using the method in accordance with the invention, the position of a medical implant, such as a cup implant, which is located in a structure, such as an anatomical body part such as for example the hip or acetabulum, is determined or measured relative to said structure without a (rigidly) attached reference array being connected directly to the anatomical body part. The position can be measured using only a reference array or reference structure which is connected to a device connected to the medical implant, in order to verify that the medical implant is correctly orientated or fitted within the structure and/or anatomical body part, wherein the measuring or verifying step can be performed with respect to at least one of the following:

1. the alignment of the medical implant with respect to a (first) reference plane of the structure, such as the anterior pelvic plane (APP);
2. the alignment of the medical implant with respect to a (second) reference plane of the structure, such as the mid-sagittal plane (MSP);
3. the position of an actual centre of rotation (COR) of the medical implant with respect to a desired or reference centre of rotation;
4. the insertion depth of the medical implant into the structure or anatomical body part, preferably with respect to a desired or reference insertion depth.

Such a device is advantageously embodied as an impactor or inserter which is used to implant or place the medical implant, wherein both the device and the medical implant preferably have an at least partially or fully known geometry which is stored in a database, and wherein the device is preferably releasably connected to the medical implant and used to place the medical implant, for example by hammering on an impact surface on the distal side of the inserter, thus driving in and/or placing the implant which is connected to the proximal side of the inserter. The impactor or inserter can be or is connected to a reference element or reference structure, such as for example a reference star comprising for example three reflecting spheres or passive markers which have a fixed relationship and/or orientation with respect to the impactor or inserter when attached to it. The geometric information regarding this fixed relationship, for example the distance and orientation of the reference element(s) relative to the medical implant, is stored in a database.

In accordance with the invention, the navigated impactor or inserter itself acts as the reference array or reference structure and is advantageously the only reference array or reference structure once a trial or final medical implant has been inserted. In the case of THR procedures, the navigated cup impactor acts as the pelvic reference array, such that no additional reference array need be connected to the pelvis or any other anatomical structure other than the reference array or elements which are connected to the impactor or inserter which is itself connected to the anatomical structure via the inserted medical implant.

Once the medical implant has been positioned within the anatomical structure and the reference element(s) attached to the impactor or inserter (which can already be attached when inserting or hammering in the medical implant), the spatial position of the medical implant can be calculated using a navigation system which determines the position of the reference element(s) and using the known predefined measured or stored relationship between the reference element(s) and the medical implant, which are both connected to the impactor or inserter.

Positional information regarding the anatomical body part(s) and/or structure(s) is acquired using for example a pointer which is known in its own right and connected to reference elements, such as the above-mentioned passive markers or reflecting spheres. The positional information regarding the structure can be acquired by determining the position of specific points or landmarks of the structure, for example by moving the tip of the pointer to these landmarks, and by acquiring their position using for example a navigation system which detects the marker(s) attached to the pointer and using the predefined relationship between the tip of the pointer and the marker(s) attached to the pointer which is for example stored in a database. In addition or as an alternative, a gyrosensor attached to the pointer can be used to track the pointer. The anatomical body part(s) and/or structure(s) can thus be considered to be at least partially registered.

The calculated position of the medical implant is compared with the acquired positions of points such as landmarks of the anatomical structure in order to determine the position of the medical implant with respect to the anatomical structure. It is then for example possible to determine, on the basis of a calculation or prior definition, whether or not the medical implant is correctly aligned within the anatomical structure or at least within specific boundaries given for the alignment, so as to verify that the implant is correctly fitted or placed or to determine that the implant is not correctly fitted, in which case the above procedure is to be repeated.

Thus, using the method according to the invention, it is no longer necessary to rigidly attach a reference array to the anatomical structure, such as a pelvis, in order to provide quantitative information regarding the alignment or fit of the implant, such as the acetabular implant mentioned. Using the method according to the invention consequently results in a significant reduction in the operating room (OR) time required, once computer-assisted surgery is applied, since attaching the bone reference array normally required usually takes about 5 to 7 minutes—time which is no longer required in accordance with the present invention. Since no bone reference array is required, the risk of a fracture on the anatomical structure, such as the iliac crest, is also eliminated, and there is also no risk of this reference array loosening once the user decides to attach it inside the incision. In addition, there is no danger of the (probably high) tissue tension moving the bone fixator of the reference array, since the latter is no longer required.

A surgeon can thus quantify the accuracy of the alignment or position of the medical implant with a minimum of effort. Moreover, the instrumentation required for the computer-aided surgery (CAS) is significantly reduced, which also reduces the costs involved. In accordance with the method of the invention, only an impactor or inserter—which can be straight or curved—is used together with reference elements or a reference structure, which are or can be connected to the impactor or inserter, in addition to which only a trackable pointer is required.

Thus, a methodology is provided for measuring the position of any medical implant during any medical procedure (primarily and/or as a revision) in 3D space without the need for references which are rigidly attached to a bone or other anatomical structure.

If the medical implant is formed so as to be axially symmetrical, as is usually the case with a cup implant, or if the orientation of the medical implant within the structure can be arbitrary about an axis, the connection mechanism between the medical implant and the impactor or inserter only has to be designed so as to fix or reliably define this axis of symmetry. In this case, any releasable connection between the impactor/inserter and the medical implant which reliably defines at least one axis, advantageously the axis of symmetry, of the implant with respect to the impactor/inserter can be chosen, such as for example a screw fastening, a snap-on connection or any connection which defines at least one axis of the medical implant when connected to said connection element of the impactor/inserter. If the orientation of the medical implant with respect to the impactor/inserter is of particular importance and has to be observed, the connection mechanism is preferably formed so as to align the medical implant in a single position or a number of defined positions with respect to the impactor/inserter, wherein the geometric relationship between the marker(s) which can be connected or are attached to the impactor/inserter and the respective defined position of the medical implant is stored in a database.

In the case of THR, the diameter of the cup implant determines the centre of rotation (COR) of the joint, which is then half said diameter. The axis of symmetry of the implant runs through the COR.

A pointer such as has been mentioned above, which is known in its own right and is connected to reference elements which can be detected by a navigation system and/or is connected to a gyrosensor, can additionally be used to track the position of the at least partially registered anatomical structure, for example if the tip of the pointer is held securely on a specific point or landmark of the anatomical structure after being registered. A (trial) medical implant can then be removed and/or re-inserted without the need to register the anatomical structure again. Alternatively or additionally, the pointer can for example be guided using the navigation system and/or the gyrosensor in order to indicate an index or reference point on the anatomical structure which should match a part or element of the impactor/inserter or the medical implant, preferably a point on an outer surface of the medical implant, in order to aid in correctly positioning or aligning the implant within the anatomical structure.

The pointer can be used to indicate a desired or correct alignment of the medical implant. For example, the tip of the pointer can be brought onto or in the proximity of the center of rotation of the medical implant and can further be aligned guided by a navigation system and/or an attached gyrosensor to show the direction the device or impactor attached to the medical implant should point. Thus, an optical aid for reinserting or realigning the device or impactor and thus realigning the implant can be provided when considering the thus correctly aligned pointer compared to the (so far not correctly aligned) device or impactor/inserter.

A computer or calculating unit which is connected to the navigation system receives data from the camera(s) of the navigation system in order to determine the position of the medical implant which is connected to the impactor/inserter bearing markers and to determine the anatomical structure which is at least partially palpated using the pointer. Said computer or calculating unit has access to a database in which structural or geometric information regarding the position or orientation of the medical implant when connected to the impactor/inserter in relation to the reference element(s) of the impactor/inserter is stored, in order to determine the spatial position of the medical implant. Using the data acquired using the pointer, the spatial position and shape of the anatomical structure is also determined. On the basis of these two determined positions—the position of the medical implant and the position of the anatomical structure—and the shape of the anatomical structure, which can also be stored as a reference shape in a database, it is possible to determine whether or not the medical implant is correctly fitted within the anatomical structure. The correct fit of the medical implant within the anatomical structure can either be defined and stored in a database as a function of the acquired position of the anatomical structure or can be calculated using the acquired positional information concerning the anatomical structure and/or the acquired or known position of an already set further implant. Further parameters which can be considered to define or calculate the correct seat of the implant can be the length of the leg, the medial/lateral offset and/or the range of motion. Deviation information which quantifies the accuracy of fit of the medical implant can be derived from a comparison between the correct position of the medical implant within the anatomical structure and the acquired or measured position of the medical implant within the anatomical structure. The deviation information can be an angle between an axis of the implant, such as an axis of symmetry, and a desired or correct reference position of this axis with respect to the anatomical structure. The angular information regarding the deviation in the fit of the implant can also be determined with respect to one or more planes, for example in the form of an angle specifying the deviation from the anterior pelvic plane (APP) and an angle specifying the deviation from the mid-sagittal plane (MSP). It is also possible to quantitatively specify the direction in which and the distance by which the centre of rotation (COR) determined for the fitted medical implant, for example by halving its diameter, is offset from a desired position calculated for example from the surface information acquired for the anatomical structure. It is also possible to determine the distance by which the medical implant deviates from a desired insertion depth of the implant within the anatomical structure.

Using predefined values, such as for example an angular deviation of 3 to 5 or 10 degrees and a positional deviation of 1 mm to 5 mm, it is possible to determine whether the fit of the medical implant within the anatomical structure is within allowable limits and is thus tolerable or whether the medical implant exceeds allowable tolerances with respect to at least one positional parameter, in which case the medical implant needs to be removed and re-positioned. The direction and magnitude of the misalignment of the medical implant can be calculated and for example displayed on a screen in order to provide a surgeon with correction information which specifies how the implant needs to be re-aligned or re-inserted in order to be correctly positioned.

If an implant has no axis of symmetry, the angle of deviation about a reference axis, such as the vertical axis, can be determined and optionally displayed in order to provide quantitative correction information.

If the anatomical structure or even the patient can be or is moved into a positionally fixed alignment, the implant can be removed from the structure, preferably using the impactor/inserter, and re-inserted, taking into account or using the above-mentioned correction information but without having to register the anatomical structure again.

It is possible to first insert a test implant, such as a trial cup, and to verify or measure the position of the inserted test implant until a correct fit or at least a fit which is within predefined allowable tolerances is achieved within the anatomical structure. The correctly fitted or inserted test implant is then removed and the real and/or final implant is definitively inserted, whereupon the verifying or measuring steps described above may optionally be performed again.

The marker or markers to be used can be any kind of conventional known markers, such as for example reflecting spheres, and can also be made of or comprise an adhesive and/or reflective material, so that the marker(s) can be attached directly to for example the anatomical structure, the impactor/inserter or the pointer. The markers can also be made of a compound or paste which is to be applied to the structure, the impactor/inserter or the pointer and is able to reflect or emit light. Any kind of marker or marker-like material can be used, as long as the marker is detectable by a navigation system such as for example a stereotactic camera.

A gyrosensor or inertial sensor such as is for example known from U.S. Pat. No. 7,559,931 B2 or DE 42 25 112 C1 can be attached to the medical implant and/or the impactor/inserter and/or the pointer, such that any movement of the implant or impactor or pointer can be detected or tracked by the gyrosensor or inertial sensor. If the output of the gyrosensor or inertial sensor is connected to the navigation system or a computer which receives data from the navigation system, the position of the medical implant and/or the impactor/inserter can be plotted or tracked once it has been located, such that the position of the medical implant or the impactor/inserter can always be determined with respect to the position of the anatomical structure, provided the anatomical structure is not moved or is itself tracked, for example by another gyrosensor.

After the medical implant is inserted into the anatomical structure, the inserter/impactor can be disconnected from the medical implant, i.e. it can for example be unscrewed from the medical implant, such that the weight of the impactor/inserter does not act on and thus strain the medical implant within the anatomical structure. One or more reference elements or reference structures can then be added to or connected to the medical implant, so that the position of the medical implant can be determined. The reference elements can for example be connected to the medical implant by screwing a reference star into the screwing connection beforehand which is used to connect the medical implant to the impactor/inserter.

The invention can be used in a so-called femur first procedure, wherein the position of an already set femur implant or stem is measured or known and the correct or desired position of the pelvic or cup implant is determined or calculated considering this position of the femur implant. Furthermore, the invention can also be used for a so-called cup first procedure, wherein the pelvic or cup implant is placed first and the stem is then positioned within the femur while also considering the position of the already set cup implant. In particular, the design of the stem, e.g. of a modular stem, can be adjusted to optimize the functionality of the joint, e.g. considering leg length, medial/lateral offset and/or range-of-motion. In all of these cases the invention can be applied to one or more implants. In particular, the invention can be used to implement a completely navigated femur or cup first workflow without need for attaching reference arrays to any of the bones.

A method in accordance with the invention is in particular a data processing method or comprises such a data processing method. The data processing method is preferably performed using technical means, in particular a computer. The computer in particular comprises a processor and a memory in order to process the data, in particular electronically. The calculating or determining steps described are in particular performed by a computer. Determining or calculating steps are in particular steps of determining data within the framework of the technical data processing method, in particular within the framework of a program. A computer is in particular any kind of data processing device. A computer can be a device which is generally thought of as such, for example desktop PCs, notebooks, netbooks, etc., but can also be any programmable apparatus, such as for example a mobile phone or an embedded processor. A computer in particular comprises interfaces in order to receive or output data and/or to perform an analogue-to-digital conversion.

The invention also relates to a program which, when running on a computer or when loaded onto a computer, causes the computer to perform one or more of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program which in particular comprises code means which are adapted to perform any or all of the method steps described herein.

A system for determining the position of a medical implant comprises a database for storing the geometric information or dimensions of the impactor/inserter or functional parts of the same, such as the connecting structures for connecting a reference element and an implant, and geometric information or dimensions of the implant itself. A navigation system for computer-assisted surgery is provided, which preferably comprises the aforementioned computer for processing the data and preferably comprises a detection device, such as a stereotactic camera, for detecting the position of detection points or markers in order to generate detection signals and for supplying the generated detection signals to the computer such that the computer can determine the position of the respective detection points or markers on the basis of the received detection signals. The computer or processor can then calculate, from the positional data received from the navigation system which includes for example the markers connected to the impactor/inserter and the markers connected to the pointer, the position or fit of the medical implant within the anatomical structure by additionally using the geometric relationship between the tip of the pointer and the markers of the pointer and the geometric relationship between the medical implant and the markers of the impactor/inserter to which the medical implant is attached, wherein said data can be stored in the database or can alternatively be separately entered by a user.

A device, such as an inserter or impactor, for positioning a medical implant, such as a cup implant, inside an anatomical structure, for example inside the acetabulum, comprises: a connecting mechanism for connecting the medical implant to one side (the proximal side) or one end of the device; a driving element or striking surface or impact surface for receiving a force exerted by a user, i.e. which is for example designed to be hit by a tool, such as a hammer, and is provided at a different or opposing side (the distal side) or end of the device; and a connection mechanism for a reference element, such as a known reference star. The connection mechanism can be a fixed connection or can be a releasable connection, such that the reference element(s) can be removed from the device.

In the following detailed description of embodiments, further advantageous features are disclosed. Different features of different embodiments can be combined.

Figure 1:
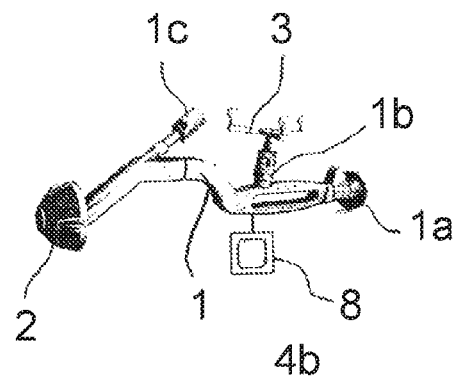
FIG. 1 shows a device for positioning a cup implant.

FIG. 1 shows a device 1 which can also be designated as an inserter or impactor and has a distal-end surface 1a onto which a surgeon can hammer in order to position or drive an implant 2, being a cup implant, into an anatomical structure, such as the acetabulum. The medical implant 2 is releasably connected to the proximal side of the device 1, for example by a screw connection. Using the device 1, a trial implant 2 can first be aligned inside the anatomical structure, before the actual implant is moved to its desired and/or final position within the anatomical structure, for example by hammering the implant into the structure. The implant 2 and the surface 1a are positioned on opposing sides of the device 1.

A reference star 3, which in the embodiment shown has three reflecting spheres or markers, is connected to the device 1 via a releasable connection 1b, such that the reference star 3 can be removed from the device 1 when the device 1 is used to hammer the implant 2 into position. Once the implant 2 has been positioned or hammered in, the reference star 3 is connected to the device 1, wherein the releasable connection 1b is preferably configured so as to ensure that the reference structure 3 has a defined orientation or relationship with respect to the device 1 and/or in particular with respect to the implant 2.

All the relevant geometric information regarding the reference structure 3 and the device 1, in particular the positional relationship between the reference structure 3 and the device 1, is stored in a database and can be accessed by the navigation system or by a computer.

A gyrosensor or inertial sensor 8 can be connected to the device 1 in order to track its position.

Figure 2:
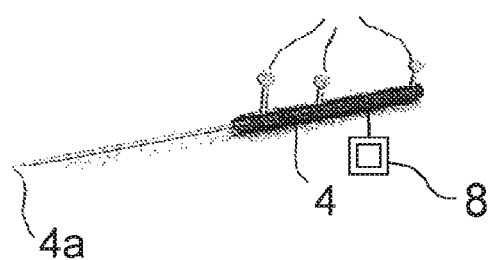
FIG. 2 shows a known pointer.

The pointer 4 shown in FIG. 2 is used to digitise defined body landmarks or specific parts of the anatomical structure by moving the tip 4a of the pointer 4 to the respective landmarks. The reference elements 4b, which are preferably fixedly connected to the pointer 4, can be detected by a reference system, such that the position of the tip 4a of the pointer 4 and thus the position of the landmark can be acquired, if the distance or spatial relationship between the markers 4b and the tip 4a is known, for example from a database.

Figure 3:
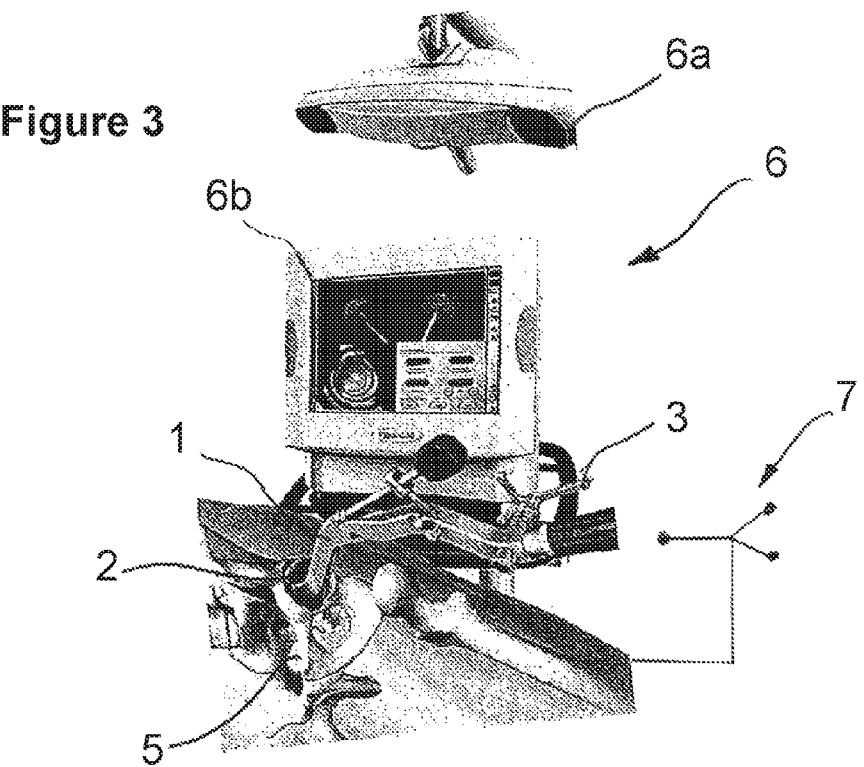
FIG. 3 shows the cup implant inserted in the acetabulum, ready to be positionally measured using a navigation system.

Once the implant 2 has been hammered into the anatomical structure 5, such as into a joint as shown in FIG. 3, both the cup implant 2 and the device 1 are in a stable relationship and have a fixed position with respect to each other. The device 1 is self-supporting due to the connection to the medical implant 2, i.e. it remains in position even when the surgeon lets go of it. This rigid system acts as a reference system and is advantageously not moved during the following steps.

The surgeon uses the pointer 4, shown in FIG. 2, to digitise relevant body landmarks of the anatomical structure 5. The centre of rotation (COR) of the joint of the anatomical structure 5 can be acquired as an additional landmark in the following way.

The diameter of the implanted cup 2 is known, as is the relevant geometric information regarding the cup inserter 1, such that the centre of rotation of the joint can be calculated and is known even after the cup 2 has been inserted, if the markers 3 connected to the device 1 are detected by the camera 6a of the navigation system 6.

Using the landmarks which have been digitised using the pointer 4, and the centre of rotation determined in this way, the relevant reference planes in the three-dimensional co-ordinate system can be created, namely the anterior pelvic plane (APP) and the mid-sagittal plane (MSP), which the anatomical directions "inclination", "declination", "anteversion" and "retroversion" refer to.

Once all the landmarks have been acquired, the navigation system 6 can display the evaluated position of the implant 2 within the anatomical structure 5 on a screen 6b. It is for example possible to indicate on the screen 6b that the deviation between the axis of symmetry of the cup implant 2 and the anterior pelvic plane (APP) is 17°, that the deviation from the mid-sagittal plane (MSP) is 42° and that the offset between the measured centre of rotation and the desired centre of rotation as derived from the digitised structural landmarks is 1 mm.

The surgeon can either accept the result, if for example the software indicates that there is no deviation or that all deviations are within predefined tolerances, or can adjust the cup inserter position on the basis of their clinical experience or by using correction information provided by the navigation system 6 or a computer connected to it.

An external reference structure 7 can for example be attached to the anatomical structure 5, the patient or an element which has a fixed positional relationship to the patient such as a table on which the patient is located, such that the anatomical structure 5 does not have to be registered again when the above procedure is repeated.

As soon as the impactor 1 is stable in the joint again, the above-mentioned procedure can be repeated.

The invention can be used in all surgical total hip replacement approaches such as direct anterior, anterior-lateral and posterior-lateral.

The invention claimed is:

1. A method for measuring a position of a medical implant relative to an associated anatomical body part using an associated inserter or impactor device operably coupled with a reference structure and having an at least partially known or previously determined geometry or at least partially known dimensions, the medical implant being axially symmetric about an axis defined by the medical implant, the method comprising:

releasably connecting the medical implant with the associated inserter or impactor device such that a relative alignment between the axis defined by the medical implant and the associated inserter or impactor device is fixed or determined and with a rotational position of the medical implant about the axis being arbitrary;

acquiring positional or landmark information regarding the associated anatomical body part by using a pointer to which a reference element, an inertial sensor, or a reference element and an inertial sensor is connected;

calculating an orientation of the axis defined by the medical implant and a position of the medical implant along the axis using a navigation system and the reference structure operably coupled with the associated inserter or impactor device; and comparing the calculated orientation of the axis defined by the medical implant and the position of the medical implant along the axis with the acquired positional or landmark information regarding the associated anatomical body part in order to measure the position of the medical implant relative to the associated anatomical body part.

2. The method according to claim 1, further comprising using the associated inserter or impactor device to move the medical implant into a desired position within the associated anatomical body part.

3. The method according to claim 1, further comprising considering the position of a further already set implant for determining a correct seat of the medical implant in the associated anatomical body part.

4. The method according to claim 1, further comprising:
determining a reference position of the medical implant based on the acquired positional or landmark information regarding the associated anatomical body part; and
comparing the calculated position of the medical implant along the axis with the determined reference position of the medical implant in order to verify the position of the medical implant relative to the anatomical body part.

5. The method according to claim 1, further comprising:
determining correction information by comparing the calculated position of the medical implant with a determined reference position of the medical implant as derived from the positional or landmark information regarding the associated anatomical body part, wherein the correction information provides quantitative information regarding deviation between the medical implant and the determined reference position.

6. The method according to claim 1, further comprising moving an external marker or marker structure into a fixed relationship with respect to the associated anatomical body part in order to act as a reference for maintaining registration of the anatomical body part.

7. The method according to claim 1, further comprising using a gyrosensor as the inertial sensor attached with the associated inserter or impactor device to provide tracking information regarding the associated inserter or impactor device and/or using a gyrosensor as the inertial sensor attached with the pointer to provide tracking information regarding the pointer.

8. The method according to claim 1, further comprising disconnecting the associated inserter or impactor device from the medical implant once the medical implant has been moved into the associated anatomical body part, and a reference element or reference structure is connected to the medical implant in order to determine the position of the medical implant.

9. A method for placing a medical implant axially symmetric about an axis defined by the medical implant in an associated anatomical body part, the method comprising:

placing the medical implant in the associated anatomical body part using an associated inserter or impactor device coupled with the medical implant such that a relative alignment between the axis defined by the medical implant and the associated inserter or impactor device is fixed or determined and such that a rotational position of the medical implant about the axis is arbitrary; and measuring a position of the medical implant by:

acquiring positional or landmark information regarding the associated anatomical body part by using a pointer to which a reference element, an inertial sensor, or a reference element and an inertial sensor is connected;

calculating an orientation of the axis defined by the medical implant and a position of the medical implant relative to the axis using a navigation system and a reference structure operably coupled with the associated inserter or impactor device; and comparing the calculated orientation of the axis defined by the medical implant and the position of the medical implant relative to the axis with the acquired positional or landmark information regarding the associated anatomical body part in order to measure the position of the medical implant within the associated anatomical body part.

10. A program comprising computer executable instructions recorded on or stored in a non-transitory computer readable medium which, when executed on an associated computer causes the associated computer to perform a method for placing a medical implant in an associated anatomical body part, the medical implant being axially symmetric about an axis defined by the medical implant, the method comprising:

acquiring positional or landmark information regarding an associated anatomical body part by using a pointer to which a reference element, an inertial sensor, or a reference element and an inertial sensor is connected; and calculating an orientation of the axis defined by the medical implant and a position of the medical implant along the axis using a navigation system and a reference structure operably coupled with an inserter or impactor device releasably connected with the medical implant, wherein the calculated orientation of the axis defined by the medical implant and the position of the medical implant along the axis is compared with the acquired positional or landmark information regarding the associated anatomical body part in order to measure the position of the medical implant relative to the associated anatomical body part.

11. A system for determining the position of an axially symmetrical medical implant relative to an associated anatomical body part, the system comprising:

a database;

a navigation system; and a processor which is connected with the database and the navigation system, wherein the processor:

acquires positional or landmark information regarding the associated anatomical body part while using a pointer to which a reference element, an inertial sensor, or a reference element and an inertial sensor is connected, and calculates an orientation of an axis defined by the medical implant and a position of the medical implant along the axis using a navigation system and a reference structure operably coupled with an inserter or impactor device releasably connected with the medical implant, wherein the calculated orientation of the axis defined by the medical implant and the position of the medical implant along the axis is compared with the acquired positional or landmark information regarding the associated anatomical body part in order to determine the position of the medical implant relative to the associated anatomical body part.

* * * * *